(12) United States Patent
Phillips et al.

(10) Patent No.: US 6,887,203 B2
(45) Date of Patent: *May 3, 2005

(54) OPHTHALMOLOGICAL ULTRASONOGRAPHY SCANNING APPARATUS

(75) Inventors: Scott Howard Phillips, Victoria (CA); Christopher Grant Denny, Victoria (CA)

(73) Assignee: Ultralink Ophthalmics Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/233,598

(22) Filed: Sep. 4, 2002

(65) Prior Publication Data

US 2003/0004416 A1 Jan. 2, 2003

Related U.S. Application Data

(63) Continuation-in-part of application No. 09/914,924, filed as application No. PCT/CA01/00008 on Jan. 5, 2001, now Pat. No. 6,491,637.

(30) Foreign Application Priority Data

Jan. 6, 2000 (CA) .............................................. 2295431

(51) Int. Cl.⁷ ................................................. A61B 8/00
(52) U.S. Cl. ..................................... 600/445; 600/452
(58) Field of Search ................................ 600/443–446, 600/449, 452, 489, 558, 459; 73/618–622, 633–634, 637, 640

(56) References Cited

U.S. PATENT DOCUMENTS

| | | | | |
|---|---|---|---|---|
| 3,821,891 A | * | 7/1974 | Collins et al. .............. 600/452 |
| 4,206,763 A | | 6/1980 | Pedersen ..................... 128/660 |
| 4,227,780 A | * | 10/1980 | Ohta et al. .................. 351/208 |
| 4,564,018 A | | 1/1986 | Hutchison et al. .......... 128/660 |
| 4,807,634 A | * | 2/1989 | Enjoji et al. ................. 600/437 |
| 4,817,432 A | | 4/1989 | Wallace et al. ............... 73/602 |
| 4,930,512 A | | 6/1990 | Henriksen et al. ..... 128/661.06 |
| 4,932,414 A | | 6/1990 | Coleman et al. ....... 128/660.09 |
| 5,331,962 A | | 7/1994 | Coleman et al. ....... 128/660.09 |
| 5,369,454 A | * | 11/1994 | Reinstein et al. ........... 351/201 |
| 5,487,388 A | * | 1/1996 | Rello et al. ................. 600/445 |
| 6,491,637 B2 | * | 12/2002 | Foster et al. ................ 600/452 |

OTHER PUBLICATIONS

Ronald H. Silverman, Dan Z. Reinstein, Tatiana Raevsky and D. Jackson Coleman, "Improved System for Sonographic Imaging and Biometry of the Cornea", J. Ultrasound Med. 16:117–124, 1997.

* cited by examiner

*Primary Examiner*—Francis J. Jaworski

(57) ABSTRACT

An apparatus for ultrasound scanning of the eye is provided comprising a virtual center translocation mechanism that facilitates precise arcuate motion of an ultrasonic transducer to maintain focal distance from the eye and to maintain normality of the ultrasound beam with surfaces of the eye. The invention also provides a radius adjust mechanism for changing the radius of ultrasound scanning to facilitate positioning of the transducer focal point on selected surfaces of the eye. Centration optics are also provided, for aligning the ultrasound transducer with the Purkinje (or other optical or geometric) axis of a patient's eye. In addition the invention provides a hygiene barrier eyeseal for protection of the patient from disease propagation.

8 Claims, 14 Drawing Sheets

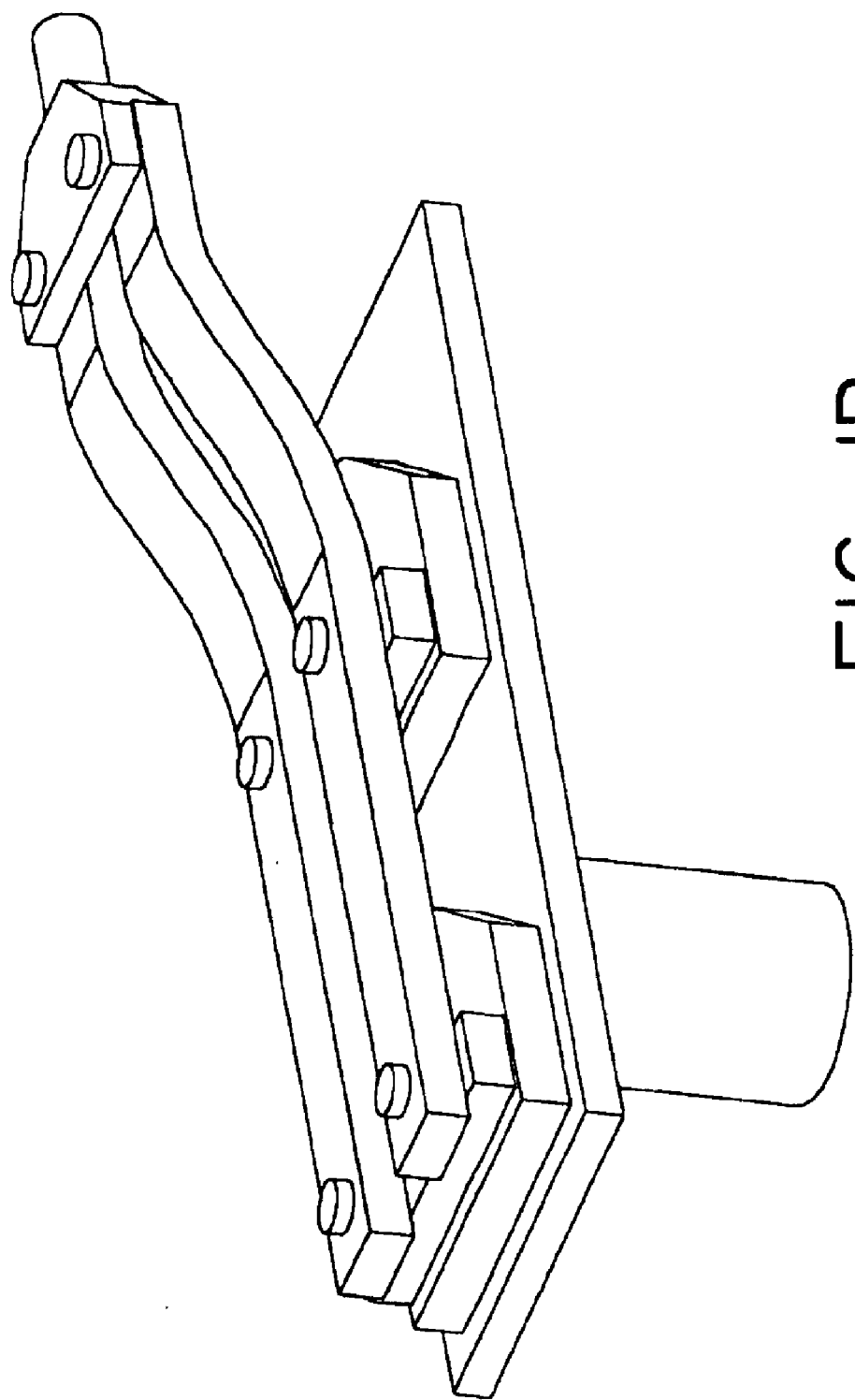
FIG. IB

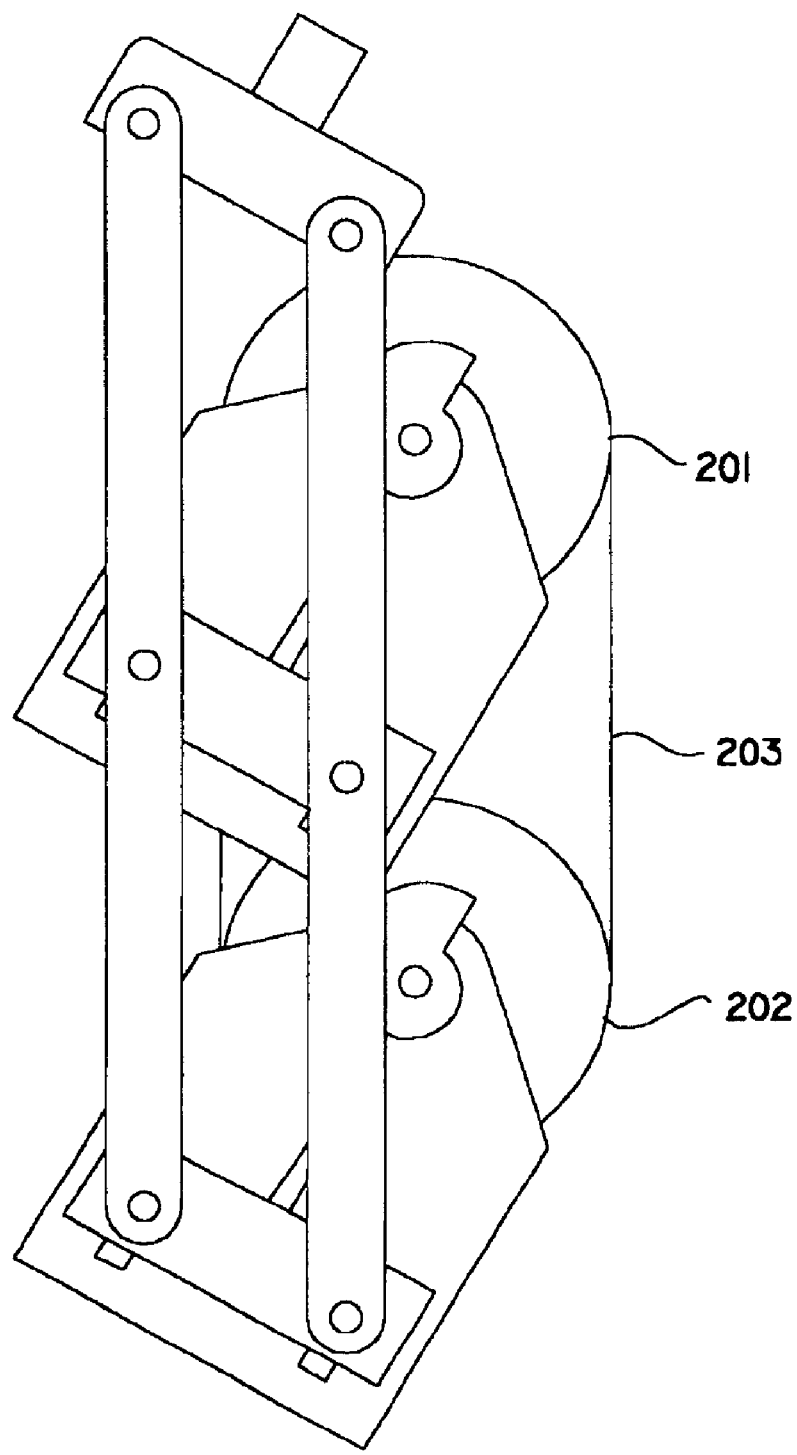
FIG. IC

A                                      B

OPHTHALMOLOGICAL ULTRASONOGRAPHY SCANNING APPARATUS

This application is a continuation-in-part of U.S. application Ser. No. 09/914,924 filed Jan. 15, 2002 now U.S. Pat. No. 6,491,637, which is a national stage PCT/CA01/00008 filed Jan. 15, 2001.

FIELD OF THE INVENTION

The invention is in the field of medical ultrasound apparatus, particularly apparatus for use in ultrasonography of the eye.

BACKGROUND OF THE INVENTION

Ultrasound may be used in a variety of medical applications, including diagnostic ultrasonography of the eye. Diagnostic information is typically provided by an ultrasound pulse from a piezoelectric transducer, which is directed into a tissue. Reflected acoustic energy is detected (as 'echoes'), so that the amplitude of the received energy may be correlated with the time delay in receipt of the echo. The amplitude of the echo signal is proportional to the scattering strength of the refractors in the tissue, and the time delay is proportional to the range of the refractors from the transducer. A variety of hand-held ultrasound instruments for measuring corneal thickness (called pachymeters) have been developed (for example see U.S. Pat. Nos. 4,564,018; 4,817,432; 4,930,512). Many prior art ultrasonic pachymeters provide A-scan output, in the form of waveforms displayed on a cathode ray tube, representing acoustic reflections in a single dimensional 'column' of tissue.

In B-scan ultrasonography, a two-dimensional image is formed, in which pixel brightness reflects the amplitude of the reflected acoustic signal. A B-scan image therefore represents a cross-sectional slice of the imaged tissue. The cross-sectional information is typically provided by correlating information from a series of adjoining columnar scans (each of which may be used to produce A-scan output). For the purpose of producing B-scans, adjoining columnar scans may be produced by a number of methods: rectilinear translocation of a transducer over the tissue of interest; pivoting angular displacement of a single transducer over a fan-shaped area; or through the use of a linear array of transducers.

In some applications, three dimensional images may be reconstructed from a series of B-scans. U.S. Pat. No. 4,932,414 to Coleman et al. for example describes a system in which the transducer is electronically swept or physically rotated to produce a series of sectored (fan-shaped) scan planes which are separated by a known angular distance, to produce a 3-dimensional display. In a similar fashion, U.S. Pat. No. 5,487,388 to Rello et al. discloses an ultrasonic scanning system in which sequential fan-shaped B-scan image planes are obtained by movement of the transducer probe in an arc, a movement which allows the apex of the scanned 3-dimensional volume to be located below the probe to facilitate imaging between closely-spaced surface obstructions.

The structure of the eye, particularly the cornea, presents special problems for optimal ultrasonographic B-scan imaging. The human cornea is an asphere, flattening concentrically, typically approximately 11 mm across with an average central radius of curvature of 7.8 mm which increases towards the periphery. The high resolution required for ultrasonic imaging of some corneal structures is optimally achieved if ultrasound data is collected from the focal point of the transducer, and the ultrasound beam is normal to the surface of the cornea. As a result, rectilinear scanning of the cornea provides optimal imaging information only from relatively small segments of the cornea which are normal to the transducer beam and in the plane of beam focus. Similarly, volumetric 3-dimensional scanning by reconstruction of a series of fan-shaped B-scan planes, as for example described in U.S. Pat. Nos. 4,932,414 and 5,487,388, is not a system adapted to provide the degree of resolution required for biometry of the corneal surface.

High frequency ultrasound has been used in ophthalmological ultrasonography to obtain biometric B-scan images of the human cornea, by arcuate translocation of a single element focused transducer. Silverman et al., 1997, J. Ultrasound Med. 16:117–124, describe a system for sonographic imaging and biometry of the cornea in which a sophisticated programmable motion system permits ultrasonographic arc scanning. In the Silverman et al. system, the ultrasonic transducer is translated through an arc matched to the approximate radius of curvature of the cornea using five servo motors and a controller. Similarly, U.S. Pat. No. 5,331,962 discloses an ultrasound system for corneal arc scanning, in which a transducer is translocated along a curved track that approximates the surface curvature of the cornea.

SUMMARY OF THE INVENTION

In one aspect of the invention, an apparatus for ultrasound scanning of the eye is provided comprising a virtual center translocation mechanism that facilitates precise arcuate motion of an ultrasonic transducer to maintain focal distance from the eye and to maintain normality of the ultrasound beam with surfaces of the eye. The arcuate movement of the transducer focal path may closely approximate the surface of the cornea. Some embodiments of the invention may include a radius adjust mechanism for changing the radius of ultrasound scanning, to accommodate different eye sizes and to facilitate positioning of the ultrasound transducer focal point on selected surfaces of the eye, such as the cornea. Centration optics may also be provided, for aligning the translocation path of the ultrasound transducer with an axis such as, but not limited to, the Purkinje axis of a patient's eye.

In one embodiment, the invention provides an ultrasound transducer support comprising a transducer mount adapted to accommodate an ultrasound transducer having a focal point. The support may be provided with a virtual centre mechanism attached to the transducer mount, for moving the ultrasound transducer along an arcuate translation path. The arcuate translation path of the transducer may be offset from a virtual centre of translocation by a radius of transducer translocation, so that the focal point of the ultrasound transducer traverses an arcuate focal path about the virtual centre of translocation. A radius adjust mechanism may be provided for adjusting the position of the transducer mount to change the radius of transducer translocation.

In an alternative embodiment, the invention provides a method of ophthamological ultrasonography comprising centring an ultrasound transducer having a focal point in alignment with the Purkinje or other optical or geometric axis of a patient's eye using centration optics, and moving the ultrasound transducer along an arcuate translation path intersecting the Purkinje or other optical or geometric axis of the patient's eye. The arcuate translation path of the transducer may be offset from a virtual centre of translocation by a radius of transducer translocation, so that the focal point of the ultrasound transducer traverses an arcuate focal path about the virtual centre of translocation.

In one aspect, the invention provides a membrane and eyeseal system that may be adapted to facilitate hygienic use of the apparatus with multiple patients. One feature of this aspect of the invention is a means for sealing the apparatus against an orbital portion of a patients' face, this may include a membrane barrier having an acoustic coupling fluid on both sides of the membrane, wherein the acoustic coupling fluids may be independently provided to the spaces on each side the membrane.

BRIEF DESCRIPTION OF THE DRAWINGS

FIG. 1B is an isometric view of an alternative embodiment of the ultrasound transducer support of the invention, showing shaped arm linkages, as are also shown in FIG. 4.

FIG. 1C is a schematic diagram showing a linking element connecting the front and rear swinging linkages which may form part of the transducer part of the invention.

DETAILED DESCRIPTION OF THE INVENTION

Figure 1A:
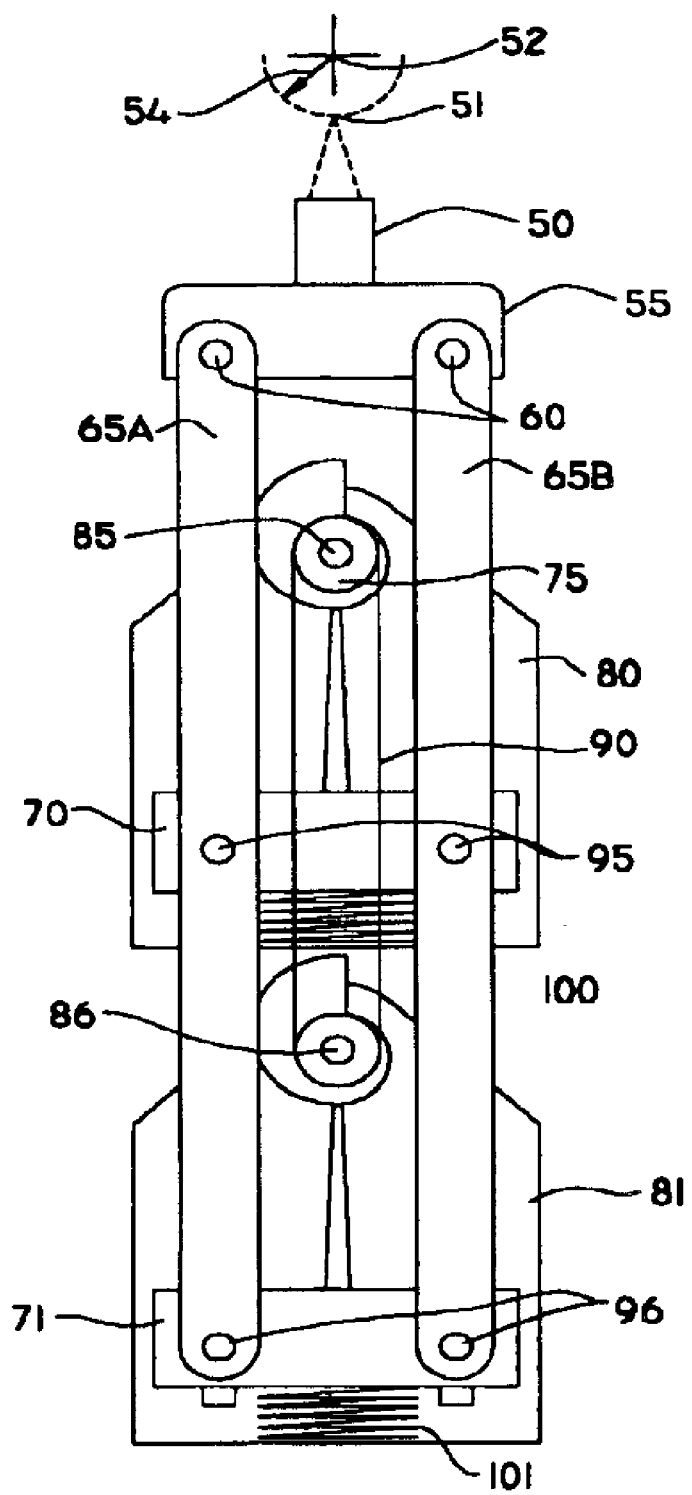
FIG. 1A is a side elevational view of an ultrasound transducer support of the invention, showing a cam-actuated radius adjust mechanism.

In one aspect, the invention provides an ultrasound transducer support comprising a transducer mount adapted to accommodate an ultrasound transducer, and a virtual centre mechanism. FIG. 1A illustrates an embodiment of a virtual center mechanism. First and second arm linkages 65A and 65B are each connected via three pivots to moving parts of the mechanism. Rear swinging pivots 96 connect first and second arm linkages 65A and 65B to rear radius adjust slider 71, and rear radius adjust slider 71 is attached to rear swinging linkage 81. Similarly, front swinging pivots 95 connect arm linkages 65A, 65B to front radius adjust slider 70, and front radius adjust slider 70 is attached to front swinging linkage 80. The front ends of the arm linkages 65A, 65B are connected by transducer pivots 60 to transducer mount 55, and transducer mount 55 is adapted to accommodate ultrasonic transducer 50. Front pivot 85 and rear pivot 86 are stationary relative to the swinging motion of front swinging linkage 80 and rear swinging linkage 81.

Figure 2:
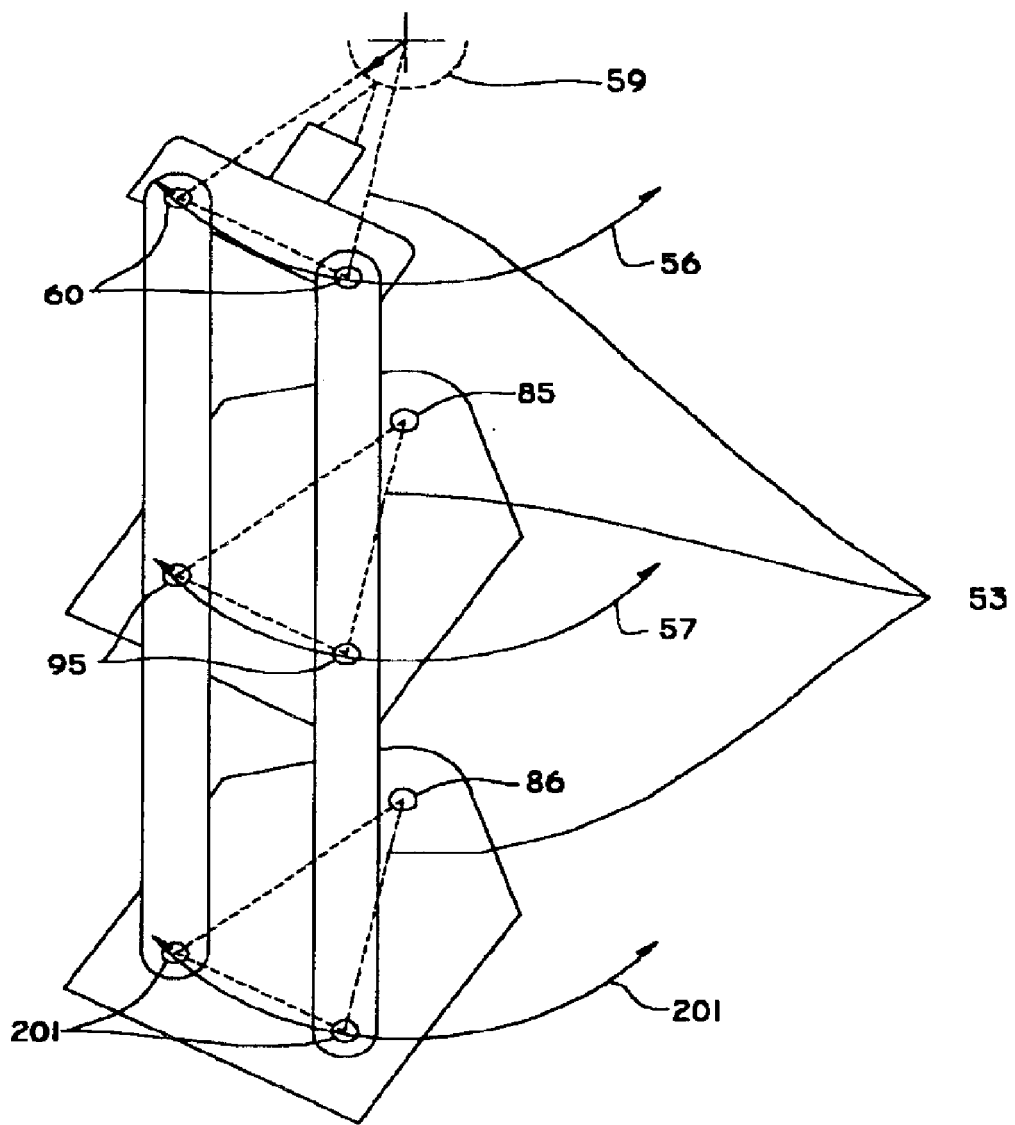
FIG. 2 is a schematic diagram showing the motion of the transducer support of the invention.
Figure 3:
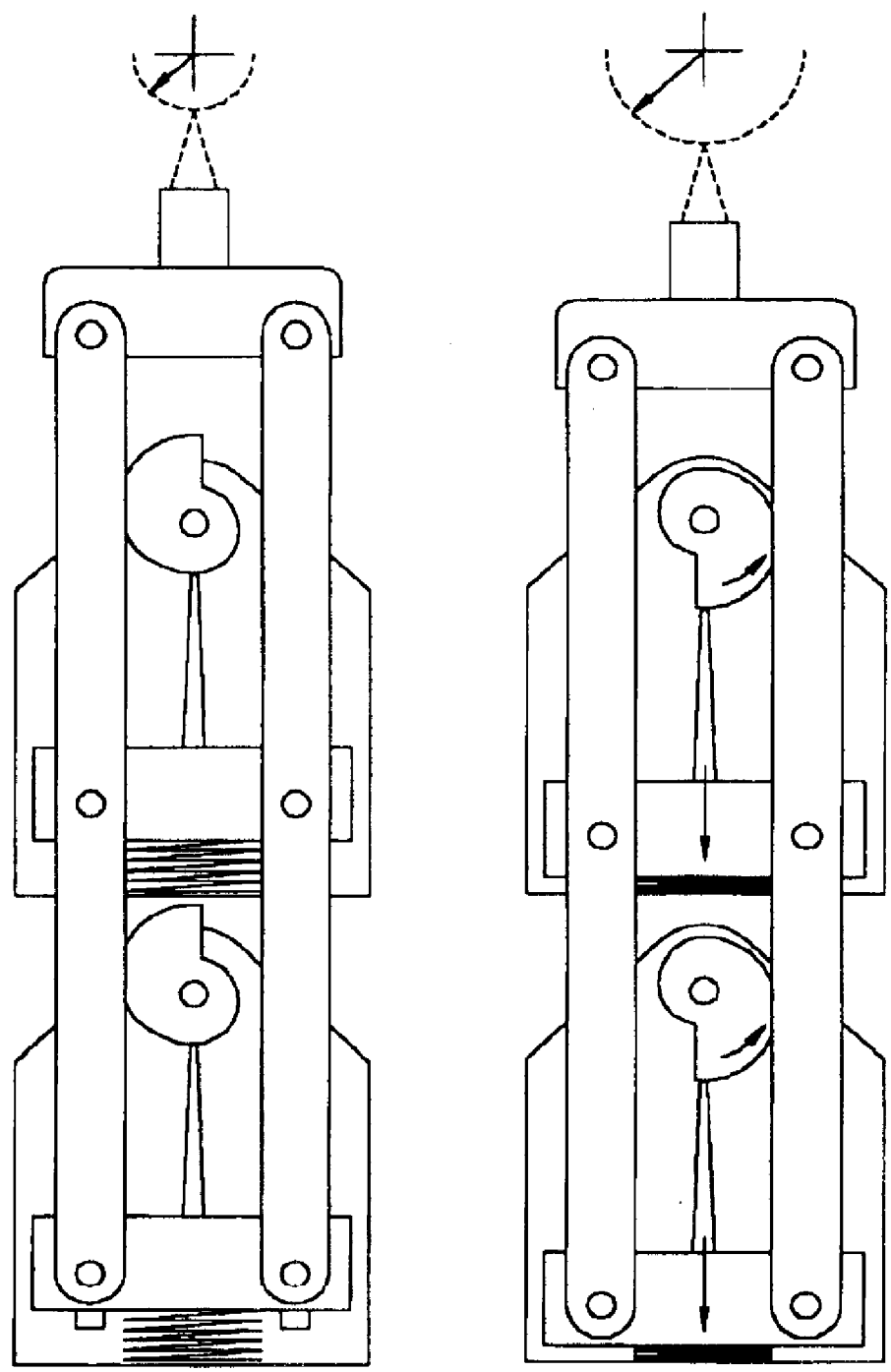
FIGS. 3A and 3B are elevations views of the embodiment of the invention shown in FIG. 1, showing the cams that are part of the radius adjust system in different positions.

The virtual centre mechanism is attached to transducer mount 55 for moving the ultrasound transducer 50 along an arcuate translation path 56 offset from a virtual centre of translocation 52 by a radius of transducer translocation, so that the focal point 51 of the ultrasound transducer 50 traverses an arcuate focal path 59 about virtual centre of translocation 52. As shown in FIG. 2, when rear swinging linkage 81 rotates about rear pivot 86, rear swinging pivots 96 describe arcuate paths about rear pivot 86. Arm linkages 65A, 65B move front swinging pivots 95, so that front swinging pivots 95 describe identical paths about front pivot 85. Similar triangles 53 show that this swinging motion causes ultrasonic transducer 50 to move in an arc such that its axis pivots about virtual center 52. In addition, transducer focus point 51 traverses an arc 59 about virtual center 52 at image radius 54. The pivoting motion of the apparatus may be driven by scanning driver 82, which may for example be a servo motor. It will be seen that focal point 51 may also lie behind virtual center 52, for example to scan the back of the eye.

The mounting of transducer 50 in transducer mount 55 may be adapted so that the position of transducer 50 is adjustable relative to transducer mount 55. Such an adjustment may be difficult to accomplish during operation, due to the configuration of the assembled apparatus, as shown in FIG. 4. A radius adjust mechanism for adjusting the radius of transducer translocation may be provided, for example by radius adjust sliders 70, 71 which are movable relative to the respective pivot points 85, 86. In operation, the effect of movement of radius adjust sliders 70, 71 is to elongate similar triangles 53. The elongation of triangles 53 reflects simultaneous changes to three radii: a 'first' radius of rotation of front swinging pivots 95; a 'second' radius of rotation of rear swinging pivots 96, and the radius of transducer translocation circumscribed by transducer pivots 60. In addition, image radius 54 is changed (the distance between virtual centre 52 and the arcuate focal path 59 traversed by the focal point 51 of transducer 50). The radius adjustment may be driven by rotating radius adjust cams 75, 76 relative to swinging linkages 80, 81. Radius adjust cams 75, 76 may be linked by a rotation linking mechanism, such as anti-backlash belt 90, which operates so that adjusting one cam automatically adjusts the other cam by the same amount. Alternatively, a single cam 75 or 76 could be used on either slider 70 or 71, in which case the other slider would follow. Mechanisms other than cams, such as motors, gears, or other mechanical linkages may be used to actuate sliding movement of radius adjust sliders 70, 71.

To provide extra rigidity to the mechanism supplementary linking such as that shown in FIG. 1C may be used. Linking element 203 may for example be a steel band or a belt or a chain or a cable and may engage sheaves 201 and 202.

Alternatively the linking may be supplied many other ways including driving both swinging linkages 80 and 81 directly with wormgears or flexures.

Figure 4A:
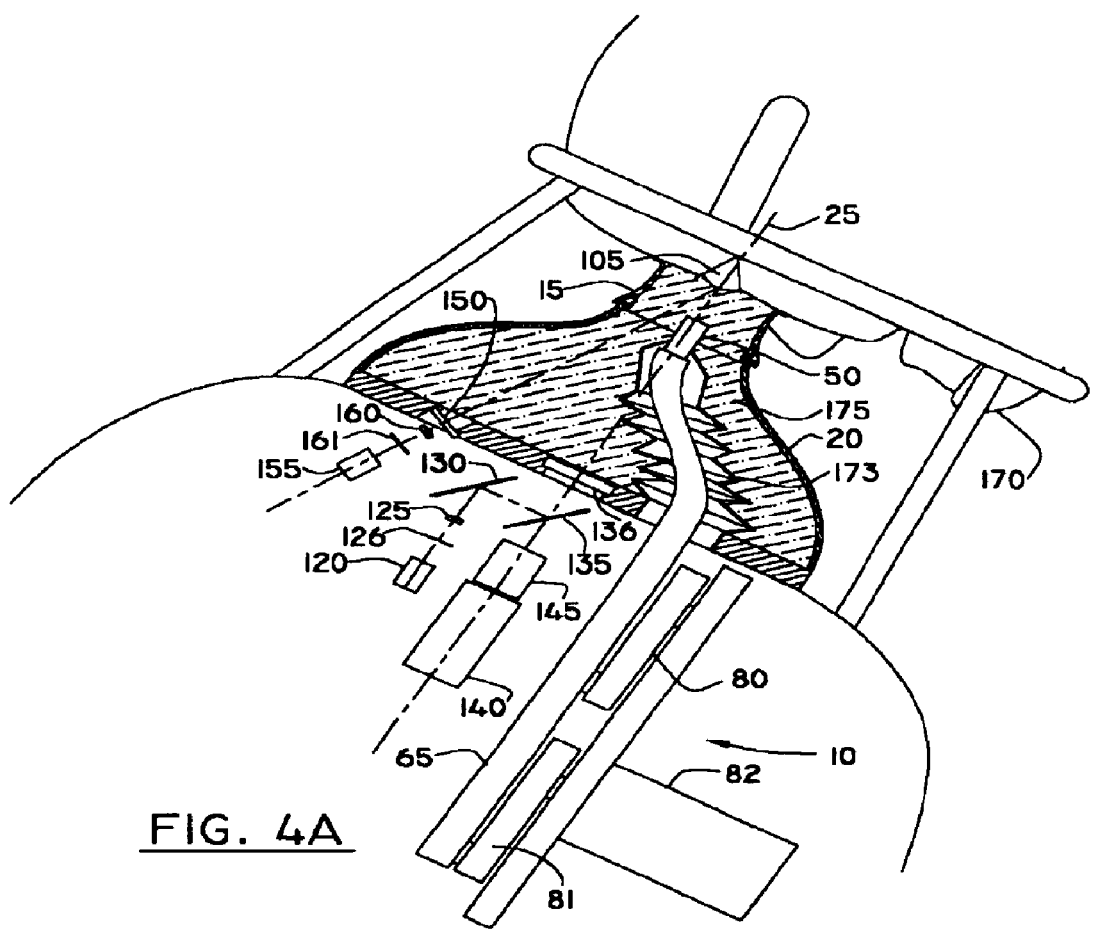
FIG. 4A is a side elevational view showing the ultrasound transducer support of the invention with accessory apparatus for sealing a fluid-filled chamber against the patient's eye.

Ultrasonic transducers for use in accordance with various aspects of the invention may be high frequency transducers, operating for example at frequencies between 50 and 100 MHz. A saline bath may be used to acoustically couple ultrasound transducer 50 to patient's eye 105. FIG. 4A shows the general arrangement of an embodiment of the ultrasound transducer support of the invention with accessory apparatus including a saline bath adapted for diagnostic use. In the illustrated embodiment, a patient may be scanned in a seated position by placing the patient's orbit against eye seal 15. The patient's head may be supported by head support 170 which may be adapted to immobilize the patient's head during ultrasound scanning. The overall axis of the apparatus, shown as line 25 in FIG. 4, may be at an angle of about 45 degrees to horizontal. Alternative angles from horizontal to vertical may also be used. In some embodiments, a patient's mandible may be supported with an upward force which encourages the teeth into mechanical contact to stabilize the patient's head. Arranging the apparatus at an overall axis of 45 degrees may help to reduce the accumulation of bubbles in the vacinity of the patient's orbit, particularly when saline fluid fills reservoir 20 and eye seal 15.

Coarse alignment of the eye on axis 25 may be done visually, for example using video camera 140, which preferably has a very high sensitivity. The seal may be tested by slowly filling the saline chamber with saline and watching for leaks. The position of the patient's head may be adjusted, or the eye seal changed, in order to achieve a good seal. Once an acceptable position has been found, the patient's head may be locked into position by immobilizing the head support. With the head stationary the scanning mechanism 10 can be moved relative to saline chamber 15 to make scan axis 25 coincident with the Purkinjie (or other optical or geometric) axis of the patient's eye.

Figure 5:
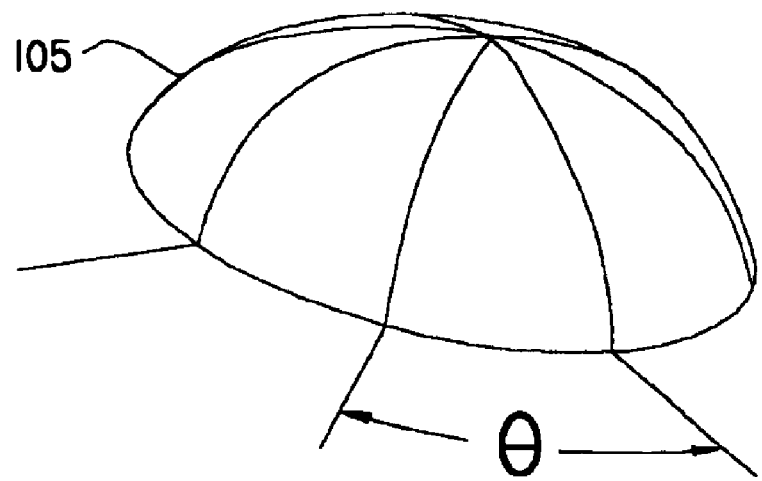
FIG. 5 is a schematic illustration of a series of meridional ultrasound scanning paths which intersect at a point near the apex of the cornea.

In accordance with one aspect of the invention, corneal scanning may be undertaken along a series of meridional paths which intersect at a point near the apex of the cornea, as shown in FIG. 5. In some embodiments, this intersection point may be the Purkinje (or other optical or geometric) axis of the eye, which may be used as an approximation of the optical axis of the eye (defined by the line between the object of regard and the fovea of the retina). The Purkinje axis may be located by shining a focused beam of light into the patient's eye, and examining the Purkinje reflections from four optical surfaces of the eye: the front and rear surfaces of the cornea, and the front and rear surfaces of the lens. The Purkinje reflections are observable along the axis of the light beam. The Purkinje axis is located when the reflections from these four surfaces are coincident. A light beam used to locate the Purkinje axis may also conveniently serve as a view target for the patient. Other axes may be used as an intersection point for meridional scanning such as the vertex-fixation axis. When a light is shone axially toward the eye onto the corneal surface, two reflected images can be seen—the specular (Normal to incident light) reflection and the diffuse reflection (not necessarily Normal reflection). When the position of the light source is adjusted such that the specular and diffuse reflections from the corneal surface are coincident, the light source will now be perpendicular to the vertix of the cornea. The vertex fixation axis is obtained when the patient's eye is looking directly at a fixation target, while observing coincidence of the diffuse and specular corneal surface reflections.

Figure 4B:
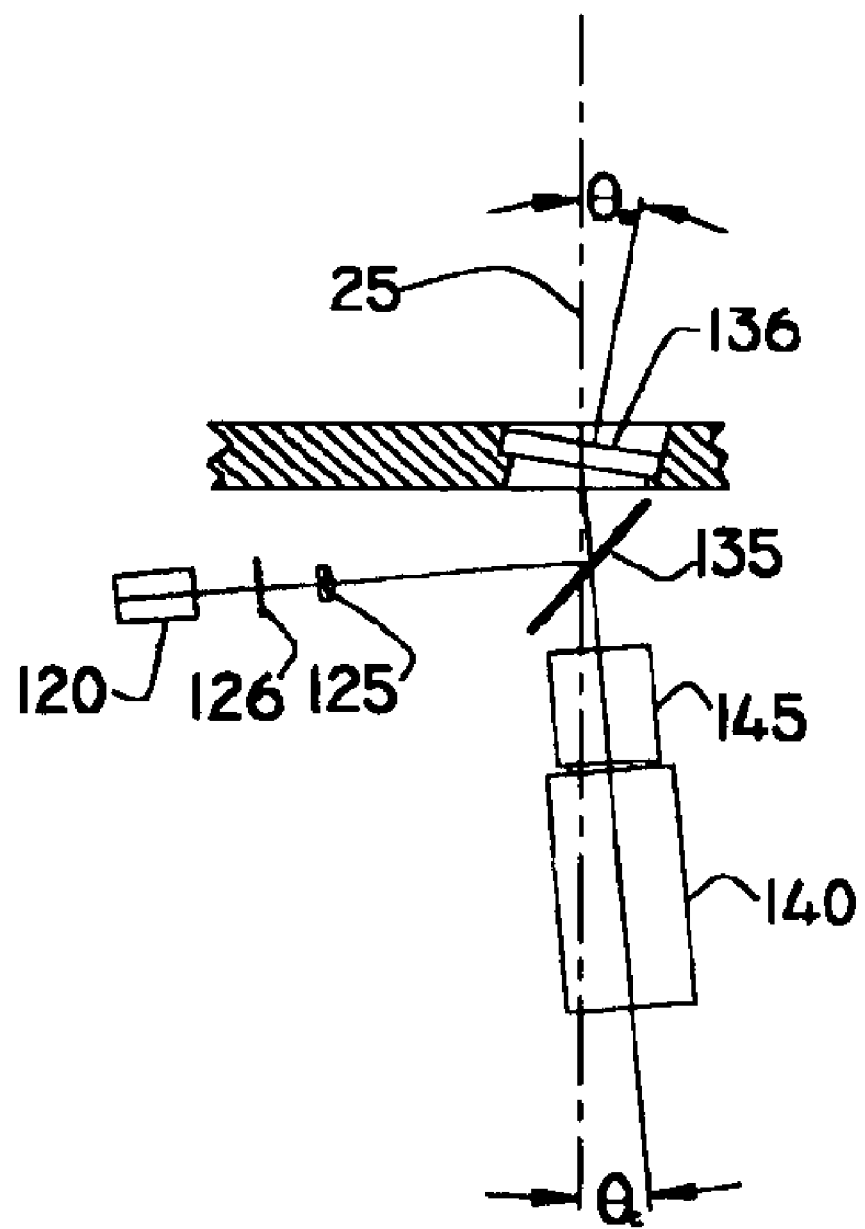
FIG. 4B is a schematic illustration showing alternative optics which may be used in conjunction with methods of centering the transducer using the apparatus of the invention.

FIG. 4A shows an embodiment that includes accessory centration optics for centering the transducer in alignment with the Purkinje axis of the patient's eye. Centration light source 120 may be refined using aperture 126 and focused using centration optics 125. Centration light source 120 may for example be a laser, laser diode, light emitting diode or incandescent source. The centration light beam may be aligned with machine axis 25 using reflector 130, such as a prism or mirror, and beam splitter 135. The centration light beam then passes through fluid-sealed camera window 136 and through the fluid (saline) in cavity 175 before reaching the patient's eye 105. As shown in FIG. 4B in order to address potential back reflection problems from window 136, both camera 140 and window 136 may be tipped relative to machine axis 25 in such a way that the centration beam still travels along the machine axis 25 within the saline chamber 175. The centration light beam thereby intersects the arcuate translation path of transducer 50. The Purkinje reflections then return back through beam splitter 135 and may be recorded by camera 140 through lens 145. As shown in FIG. 4, in order for the light to reach the patient's eye 105, transducer 50 must be swung over to the side as shown in FIG. 2. During an ultrasound scan, because the centration light beam intersects the arcuate translation path of transducer 50, the patient using the centration light as a view target will see the light disappear momentarily as the light is blocked by the passing transducer. This flashing behavior may be helpful in facilitating alignment of the eye, since the photoreceptors in the retina would otherwise saturate after a few seconds of staring at a fixed target light which may cause the eye to shift slightly to compensate.

FIG. 4A also illustrates focus point illuminator 155, which shines through focus point optics 160 and aperture 161 to produce a focus point spot on eye 105. The angle of focus point illuminator 155 is set so that when the focus point spot is appropriately positioned on the eye, the transducer apparatus is in a selected vertical position at a known distance from eye 105. The centration optics may for example be used to determined when the focus point spot joins the Purkinje (or other axis) reflections from the centration light 120. In some embodiments, this positioning of the focus point spot may be used to identify the point at which the apparatus of the invention is positioned at the correct distance from the eye to have the cornea within the focal point of transducer 50.

For extra illumination to improve the eye image on camera 140, an infra-red light may be shone through either of windows 136, 150, in which case the camera will be adapted to be sensitive to the wavelength selected.

Figure 6:
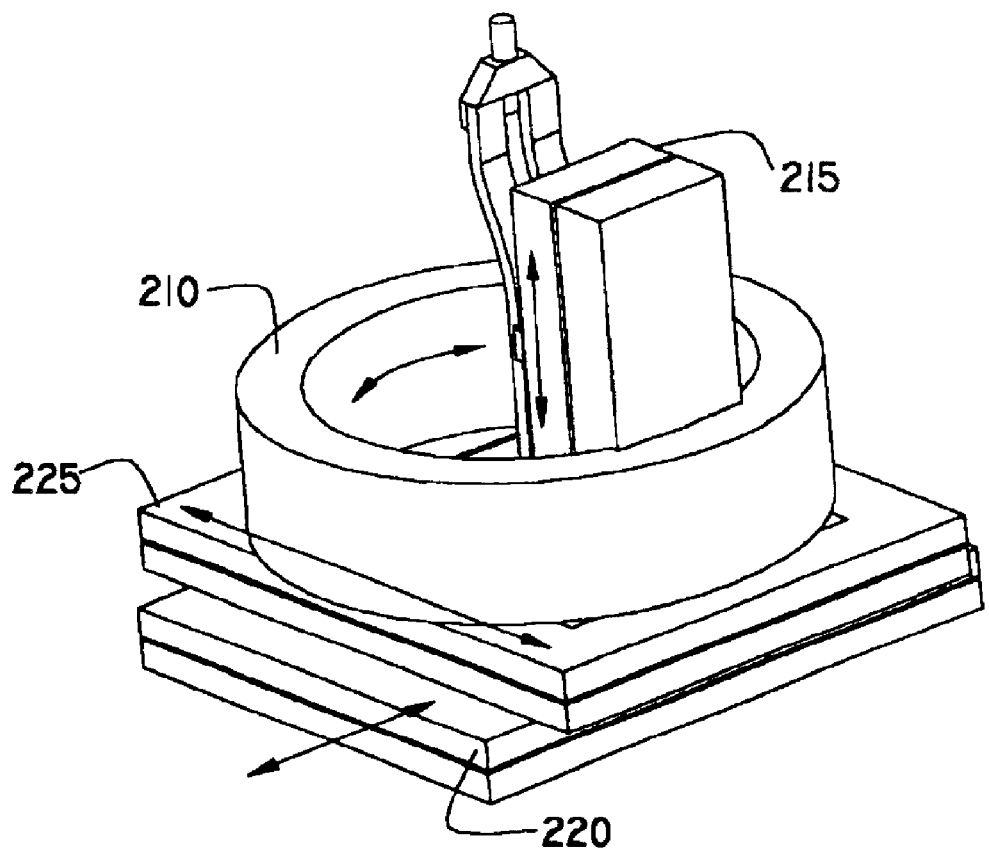
FIG. 6 is an isometric view of a stage for the scanning apparatus of the invention, providing for rotational movement of the scanning apparatus, as well as movement in X, Y and Z axes.

In addition to the scanning motion shown in FIG. 5, several other motions may be produced by the mechanism of the invention to scan an eye. In order to produce various meridian angles theta as shown on FIG. 5, the scan mechanism 10 may rotate about the machine axis 25 (shown in FIG. 4). Rotational motion of the scanning apparatus may be accomplished using rotary table 210. Motion in the Z axis, which shifts the mechanism toward or away from the eye, may be used to compensate for the degree of insetting of a patient's eye. Motion in the Z axis may be accomplished using a Z-slide 215, which may be motorized or manually controllable. Motion along the X and Y axes, perpendicular to the machine axis 25, may be used to adjust the position of the ultrasound scanning apparatus once a patient has been positioned in front of the machine. These motions may be produced by X slide 220 and Y slide 225. In some embodiments, the X and Y slides may be motorized to facilitate X and Y motion of the scanning apparatus in planar scans of eye structures, such as the iris plane. These axes may of course be arranged differently than shown in FIG. 6 while retaining the same essential operation.

Figure 8:
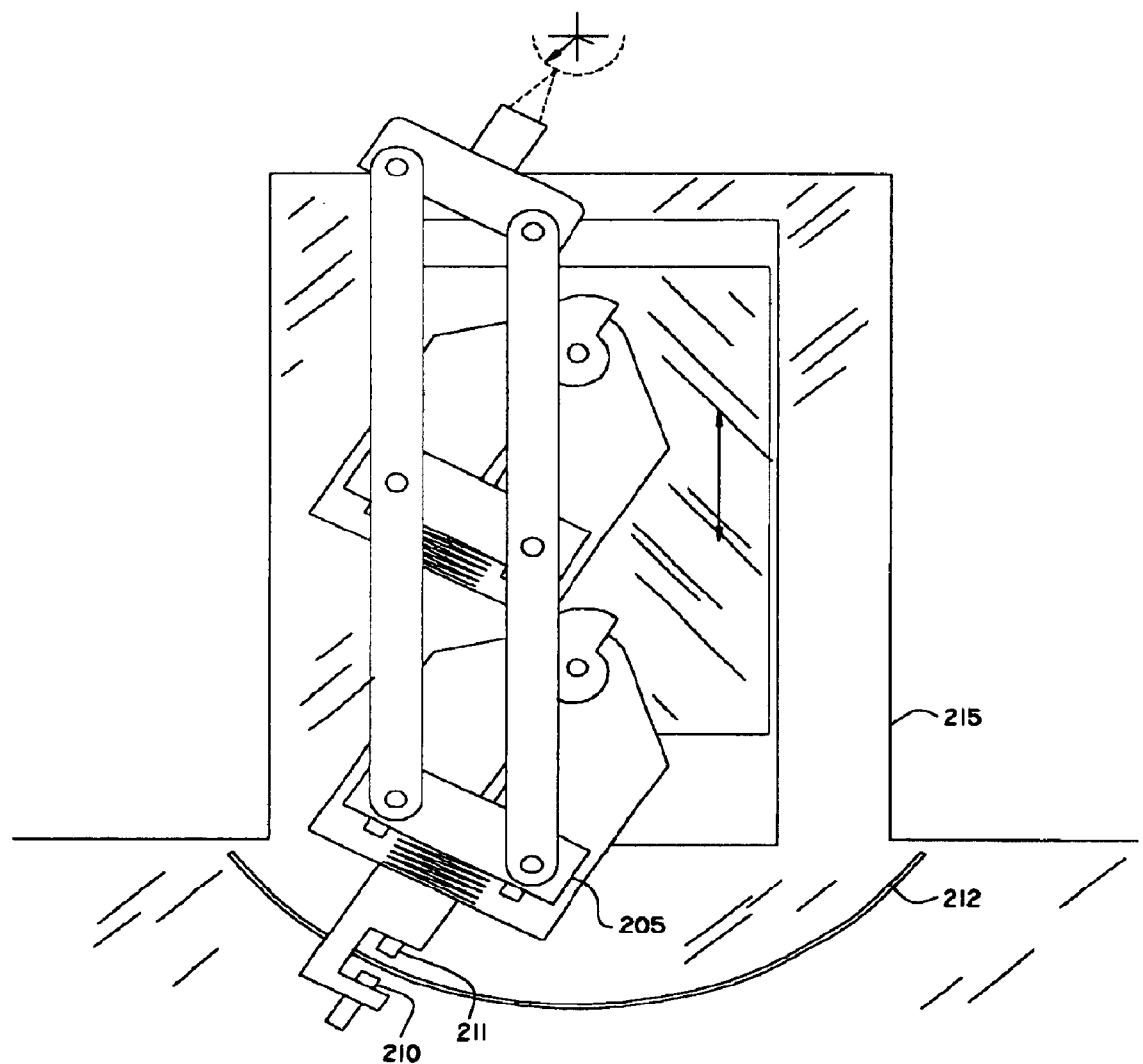
FIG. 8 is an elevational view showing a mechanical safety stop mechanism.
Figure 9:
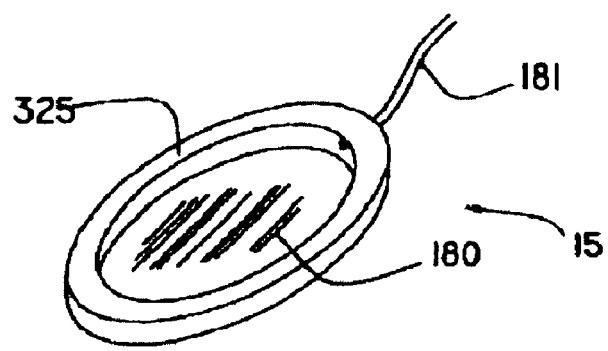
FIG. 9 is an isometric view of an embodiment of an eye seal, using a foam ring, membrane and tube.

In order to provide a mechanical means of preventing the transducer from approaching an eye too closely, a safety stop as shown in FIG. 8 may be used. The transducer may be shifted closer to the eye by either a radius adjustment or Z axis adjustment. A curved stop bar 212 may be fixed to the body of the Z axis stage 215. Stop pads 210 and 211 are fixed to radius adjust slider 205 so that an excess motion of either the radius or Z axes causes one of the pads to touch the stop bar. These stop pads 210, 211 may be supplemented with sensors for operator feedback.

Figure 7:
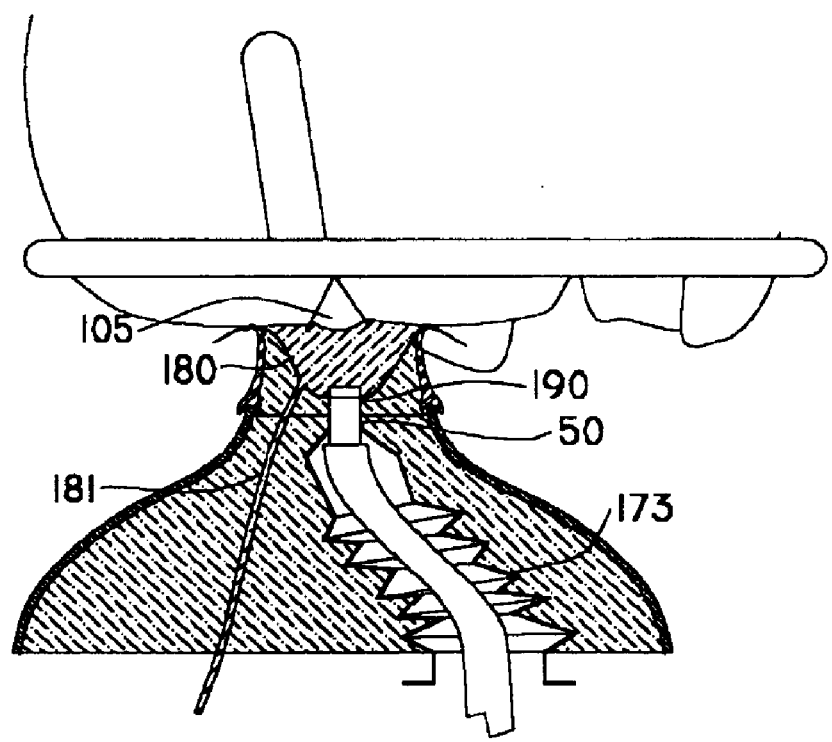
FIGS. 7 and 7A are cross-sectional side views showing a membrane which may be used in some embodiments to isolate a volume of fluid around a patient's eye.

In some embodiments, it may be desirable to provide a barrier to inhibit the passage of an infection from one patient to another. In some embodiments, it will be necessary for the centration light beam and the Purkinje (or other axis) reflections to pass through such a barrier without significant shifting or distortion. In one embodiment, membrane 180 as shown in FIG. 7 may be used, which has saline fluid on both sides of it and is selected to have a similar index of refraction to saline so that light rays passing through membrane 180 will be affected very little by its presence.

In alternative embodiments, the fluid on both the eye chamber 340 side and the transducer chamber 342 side need not be saline and may be another coupling fluid or gel. These fluids need not be the same. It may be preferable for example to have the fluid in the transducer chamber 342 contain biocide agents such as hydrogen peroxide which kill bacteria which would tend to grow inside the scanning apparatus. In some embodiments, this fluid does not need to be selected so that it is comfortable when exposed to a patient's eyes, since it is normally not in contact with the eye. The fluid in the transducer chamber 342 may not be salinated in order to reduce corrosion of the scanning instrument although there is a small difference in the speed of sound between salinated and fresh water which may affect image accuracy. The fluid in the eye chamber 340 may be saline for comfort due to the osmotic pressure of the salt ions but may also have additives which tend to kill harmful bacteria and viruses without being uncomfortable to the eye.

An additional membrane property that may be desirable in some embodiments, is that the membrane transmits ultrasonic signals from the transducer to the eye and back with minimal signal reflection. For this purpose there should be good matching between the speed of sound in the membrane material and in the surrounding fluids. Secondly the membrane 180 should not distort optical signals. If the membrane is thin, optically transparent, and has a similar index of refraction to the coupling fluids, then optical signals such as images of the eye and eye centering target images can be transmitted through the membrane with minimal distortion.

In addition the membrane 180 may be constructed of a material that allows the membrane to act as a barrier for the passage of disease causing agents such as bacteria and viruses. In some embodiments, polyethylene may be used to make a suitable membrane, other polymers that may be adapted for this use include vinylidene chloride and polyurethane.

In order to use the membrane in some embodiments, it may be mounted in a holder which allows the two reservoirs of coupling fluid to be defined. There are various ways of accomplishing this task. An eyeseal element 15 can be defined which has the membrane 180 attached to it such that the membrane is disposable and the eyeseal 15 can be sterilized between patients. Alternatively the eyeseal 15 can be disposable along with the membrane 180. Preferably the eyeseal 15 is a disposable component.

A fillable chamber (or 'eye chamber') 340 between the eye 105 and the acoustically transparent membrane 180 is an element which allows a continuous ultrasonic transmission path. This chamber could potentially be created by a variety of means including sealing the membrane 180 directly against the face 350, using a foam or elastomer element between the face 350 and the membrane 180 or having the membrane 180 attached to an inside surface of an eyeseal component 15. At the patient contact surface, a seal must be created so that excess fluid does not leak out. This seal could be a deformable element backed with a rigid structure such as used in many swimming goggles. Alternatively the seal could be a deformable foam or elastomer element, which may for example be attached to the face with an adhesive. In some embodiments, the seal element serves a double function in creating the eye chamber. In the embodiment shown in FIG. 10 a rigid eye support 330 provides a structure for a deformable eyeseal 15.

In order to fill the eye chamber 340, means may be provided for getting the acoustic coupling medium into the eye chamber 340. This filling mechanism may be a tube 181 inserted through the wall of the chamber for example. Sealing between the chamber wall and the tube 181 can be accomplished with an adhesive 321. Alternatively, a compressible tube could be inserted between the eyeseal 15 and the patient's face 350. When the chamber is being filled with acoustic coupling fluid, the air in the eye chamber 340 will be displaced by the incoming fluid and may therefore be provided with an exit. Imperfections in the seal may allow the air to escape between the patient's face and the eyeseal components. Alternatively, the eye chamber element may have an air purge valve, such as a one way check valve or a manually operated valve to allow air egress. In alternative embodiments, a material may be used for the seal with small pores, such as open-celled foam, which would allow the air to escape while preventing excessive passage of coupling medium.

In some embodiments, the component which seals against the face may be sufficiently deformable to facilitate conformation of the seal to the contours of the faces of different patients. Open-celled foams having this property may for example be used. Viscoelastic foams are a class of open celled foam which may provide particularly good deformation properties in some embodiments. In order to minimize the escape of fluids from the eye chamber 340, it may be useful to coat the wetted surfaces of the foam with a sealant 322, such as a vinyl sealant. The sealant 322 may be coated on the seal material in such a way that air flow in and out of the foam is not prevented. In one embodiment, the sealant may be applied to the top, bottom, and inside faces of a foam ring 325, leaving the outer surface 329 free for air flow in and out of the foam. Alternatively, the whole foam component 325 may be coated with sealant, and holes may later be provided through the coating. In a still further embodiment, the foam component 325 may be molded with a self skinning foam and vent holes may then be created.

In a further embodiment the eyeseal 15 may be an inflatable ring which is charged with fluid, such as a liquid water or a gas such as air. In an alternative embodiment eyeseal 15 may have a channel around the surface which contacts the face which can be suctioned onto the face using vacuum.

In addition to sealing to the face, eyeseal element 15 may be adapted to seal to the instrument to prevent the egress of fluid. This seal may for example be produced in a variety of ways including adhesives, compressible seal elements such as O-rings or gaskets, clamping with an external ring, or stretching an elastomeric eyeseal component against a rigid element on the instrument.

Figure 10:
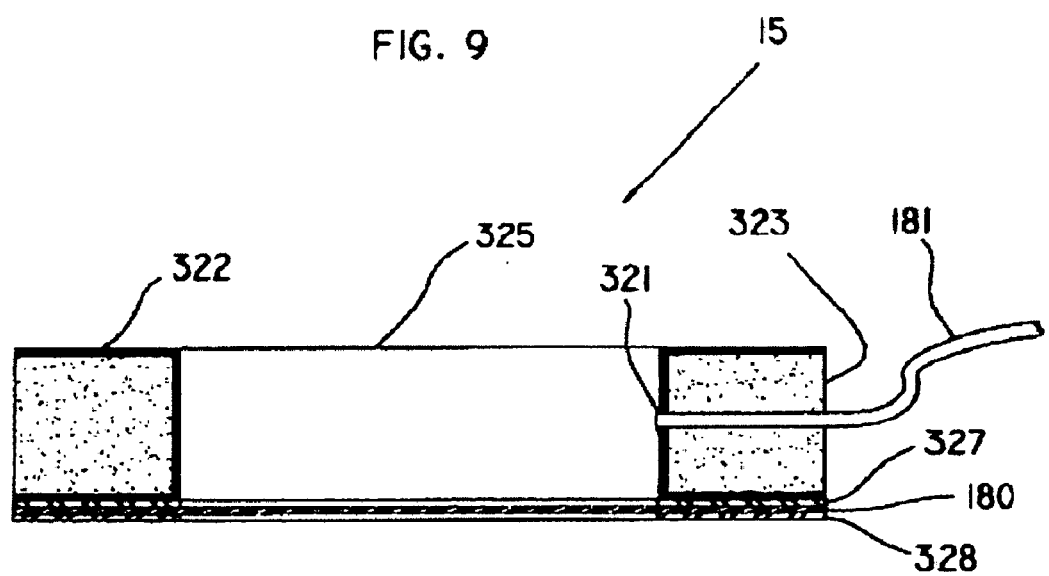
FIG. 10 is a cross sectional schematic view of an eye seal showing an embodiment having a sealant coated foam ring.
Figure 11:
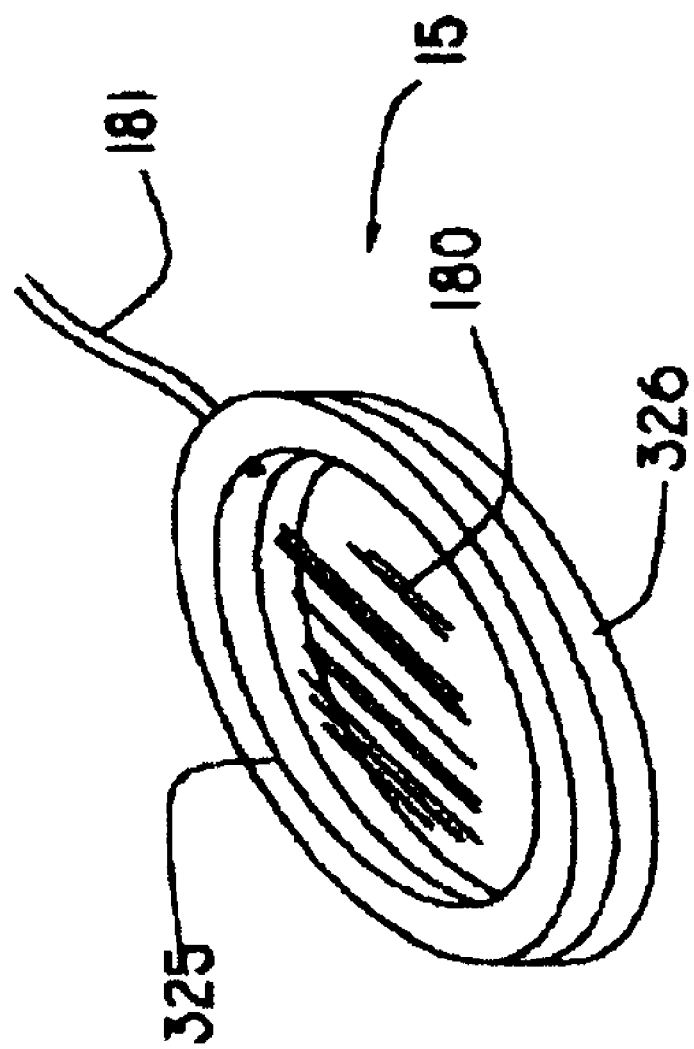
FIG. 11 is an isometric view of a double foam ring embodiment of an eyeseal of the invention.
Figure 12:
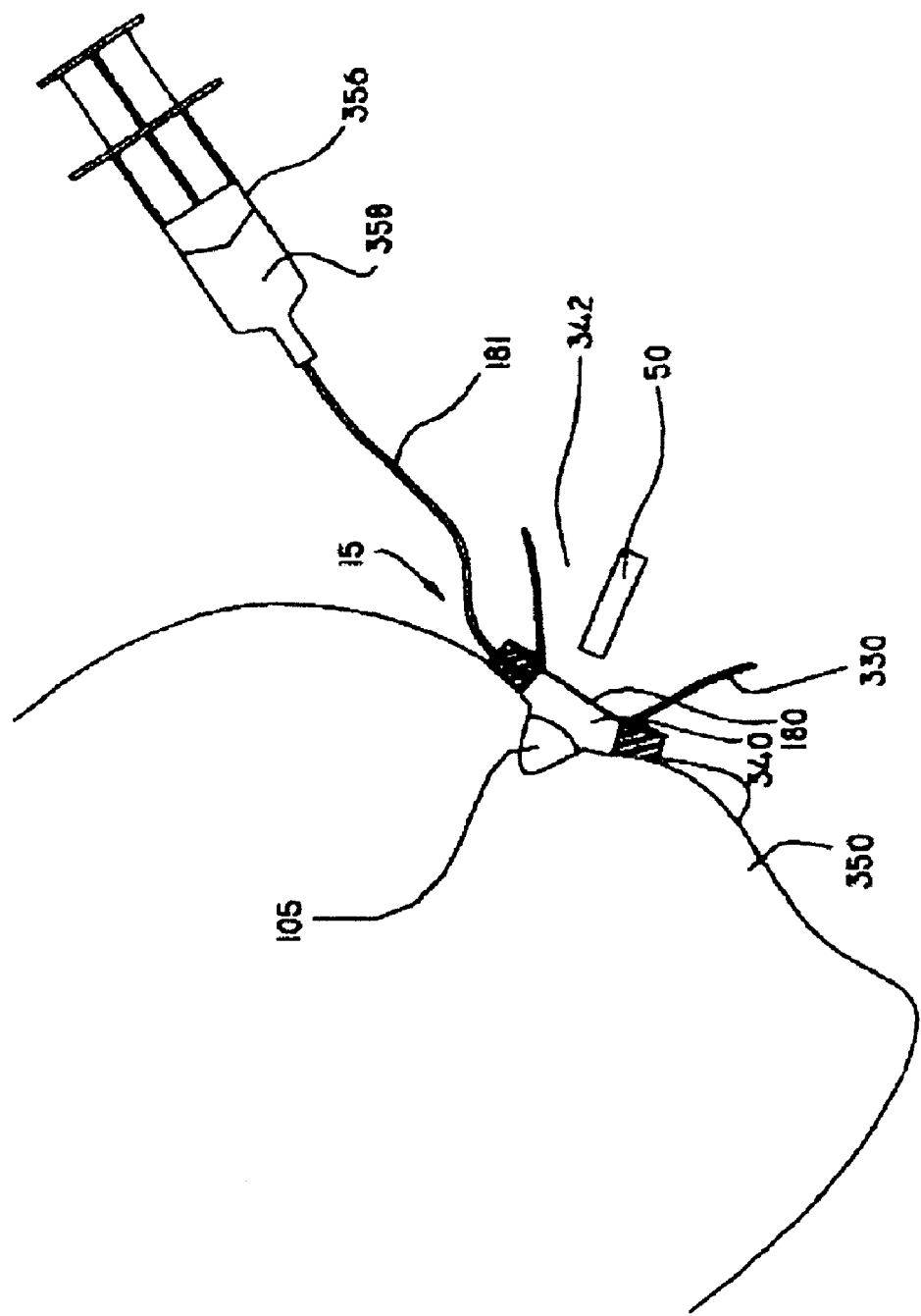
FIG. 12 is a schematic representation of a sealant-coated foam eyeseal of the invention.

In the embodiment shown in FIG. 10, membrane 180 is adhered to a ring of compressible material such as foam which provides a sealing connection to the face around the eye. This sealing ring 325 further serves to provide a chamber adjacent to the eye 105 of sufficient volume to minimize contact of the membrane 180 with the eyelashes. In addition this ring 325 provides a mounting location for a filling tube 181 which can be used for filling the eye chamber 340 with coupling fluid. Adhesive 327 may be applied between the ring 325 and the membrane 180. This adhesive must be biocompatible since it is in contact with a fluid in contact with the eye. Appropriate adhesives are commercially available. In addition, adhesive 328 may be applied to the back surface of membrane 180 in order to attach eyeseal 15 to eye support 350. Adhesive 328 may be a contact adhesive and may be selected to provide a seal against the flow of liquid water.

In embodiments where membrane 180 is close to the eye 105, it may be preferable for the membrane 180 to bulg away from eye 105, in order to reduce contact with the patient's eyelashes. This bulging form may be produced satisfactorily by mechanical deformation of the membrane.

Depending on the orientation of the instrument, there may be problems caused by air bubbles forming on the transducer 50 side of the membrane 180. An additional ring 326 of open cell foam may accordingly be provided on that side of the membrane 180, so that air bubbles can escape. Alternatively, a simple valve or other venting arrangement such as a slit or hole in the rear ring or eyeseal may be used to provide this function.

Figure 13:
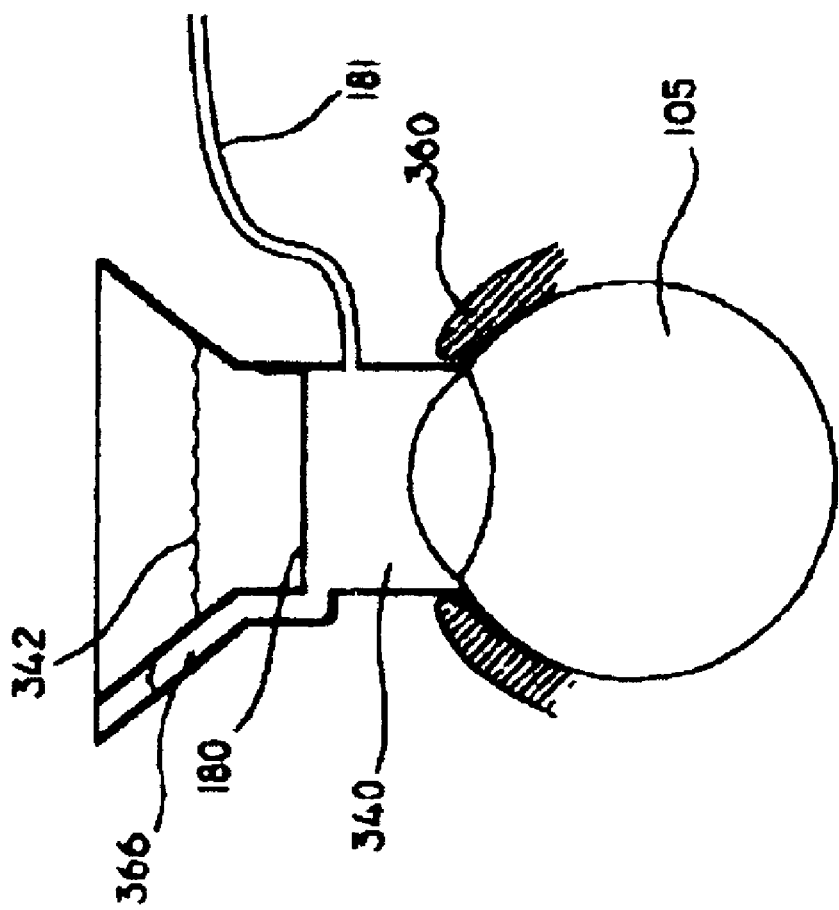
FIG. 13 is a cross sectional view of an alternative embodiment of an eyeseal, using a cup which touches the eye surface.

In an alternative embodiment shown in FIG. 13, eyeseal 15 is a cup which is designed to fit directly onto the eyeball 105 with a flange under eyelids 360. Membrane 180 may be attached to eyeseal 15 in such a way as to provide a separation of the eye chamber 340 and the transducer chamber 342. Air displaced while filling through tube 181 may escape by means of vent 366. This embodiment of the membrane barrier eyeseal may be particularly well suited for use with an alternate type of scanner in which an oscillating probe is brought to the patient.

Figure 7A:
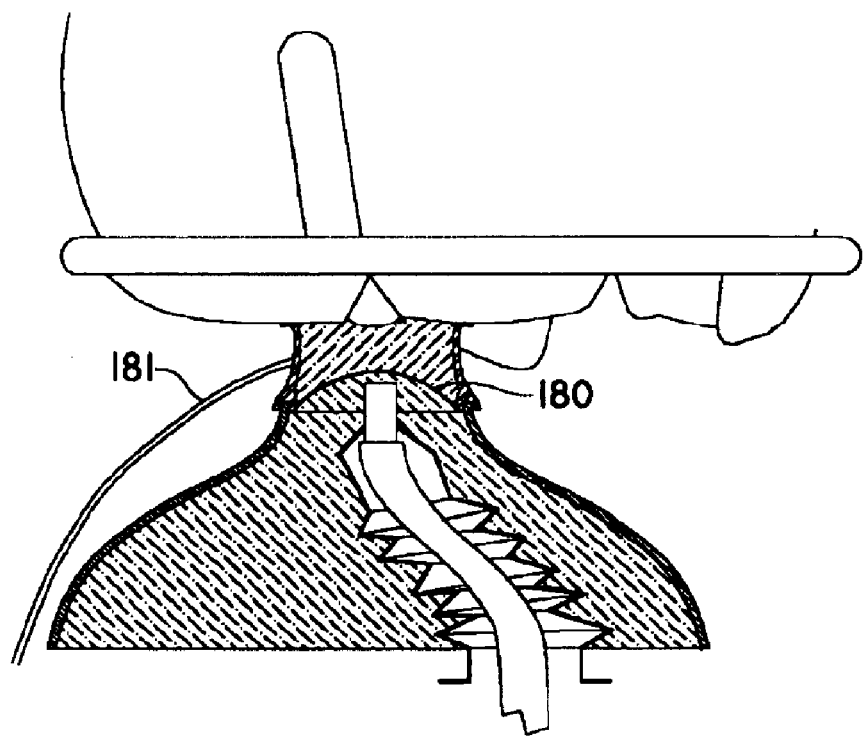

A filling and draining system may be provided, as shown by tube 181 in FIG. 7. The outer edges of the membrane 180 may be draped over the eye seal and provide the sealing surface for the face. Near its center membrane 180 may be attached by clamp 190 to transducer 50. Clamp 190 may be adapted to accommodate rotation of transducer 50 relative to the eye seal 15 during a scan, for example by permitting rotational movement of transducer 50 within clamp 190. Alternatively, membrane 180 may be continuous, and adapted to permit transmission of ultrasonic vibrations through the membrane itself as shown in FIG. 7A. In some embodiments, bellows seal 173 may be provided over ultrasound transducer 50 and linkage arms 65A, 65B.

The reservoir 356 and filling system for filling the eye chamber 340 with fluid may be a pressure system such as a squeezed fluid bag or a gravity reservoir, as are commonly used for intra venous administration of medications. Such systems may be adapted to have the advantage of automatically making up for losses due to leakage due to their relatively constant hydrostatic pressure. Alternatively the filling system may be a pumping system such as a syringe. A syringe or alternative pumping system may be adapted to provide the added benefit that fluid may be added or withdrawn in order to adjust the position of the membrane 180 relative to the eye 105. In some cases, reduplication echoes may occur in an ultrasound in which multiple images of objects appear at regular intervals due to multiple signal reflections between the transducer 50 and the objects. In particular, a second image of the membrane 180 may appear in the middle of the eye data. Providing the ability to move the membrane 180 allows such images to be shifted out of the region of interest. In addition, membrane 180 may sometimes reflect back an image of the centration light 120 into camera 140 and thus impede proper viewing of the eye 105. Shifting the barrier 180 may allow these reflections to be removed from the region of interest. Typically, the fluid in the eye chamber 340 would be sterile, and filling reservoir 356, tube 181 and any required fittings would be disposed of between patients.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to".

What is claimed is:

1. An ultrasound transducer support comprising:
   a) a transducer mount adapted to accommodate an ultrasound transducer having a focal point positioned to examine a patient's eye;
   b) a virtual center mechanism attached to the transducer mount for moving the ultrasound transducer along an arcuate translation path offset from a virtual center of translocation by a radius of transducer translocation, so that the focal point of the ultrasound transducer traverses an arcuate focal path about the virtual center of translocation;
   c) a radius adjust mechanism for adjusting the position of the transducer mount to change the radius of transducer translocation; and
   d) centration optics for centering the ultrasound transducer in alignment with an optical or geometric axis of the patient's eye, wherein the centration optics comprise a centration light source defining a centration light beam.

2. The ultrasound transducer support of claim 1 further comprising a camera for general operator feedback and for sensing reflections of the centration light beam from patient's eye for fine alignment.

3. The ultrasound transducer support of claim 2 further comprising a beam splitter for superimposing the centration light beam on a camera view.

4. The ultrasound transducer support of claim 3 further comprising an infra-red light for extra illumination to improve an image of the patient's eye image on the camera.

5. The ultrasound transducer support of claim 2 wherein the camera is adapted to be sensitive to a wavelength of infra-red light selected.

6. The ultrasound transducer support of claim 1 wherein the centration light beam is flashed to enhance immobilization of the patient's eye.

7. The transducer support of claim 1 in which a main axis of the transducer mount is tilted at an angle from the vertical in order to reduce the likelihood of trapped air bubbles.

8. The transducer support of claim 7 in which the angle is between 30 and 60 degrees from the vertical.

* * * * *